ST. AUGUSTINEGRASS

Filed Oct. 2, 1973

United States Patent

Plant Pat. 3,698
Patented Apr. 1, 1975

3,698

ST. AUGUSTINEGRASS

Jake T. Gruis, Apopka, and Terrance P. Riordan, Altamonte Springs, Fla., assignors to The O. M. Scott & Sons Company, Marysville, Ohio

Filed Oct. 2, 1973, Ser. No. 402,716
Int. Cl. A01h *5/12*
U.S. Cl. Plt.—88 1 Claim

ABSTRACT OF THE DISCLOSURE

A perennial St. Augustinegrass having a moderate olive green color, a dwarf growth habit, a fine texture, a resistance to brownpatch and a very good overall appearance. This genotype possesses moderately vigorous stolon growth and is propagated vegetatively.

SUMMARY OF THE VARIETY

This invention relates to a new and distinct perennial St. Augustinegrass selected from a series of $F_2$ generation selfs of a purple stigma diploid parent (Ea611081). This purple stigma self was labeled 45176 and propagated vegetatively by stolons to provide planting stock for studying performance and comparison to present commercial varieties.

The fine texture, good overall appearance, brownpatch (*Rhizoctonia solani*) resistance, and dwarf growth habit of 45176 along with other information allow this genotype to be distinguished from other St. Augustinegrasses including the dwarf 73176, the subject of our copending application S.N. 402,717 filed of even date herewith.

BRIEF DESCRIPTION OF THE ILLUSTRATIONS

DETAILED DESCRIPTION OF THE VARIETY

Figure 1:
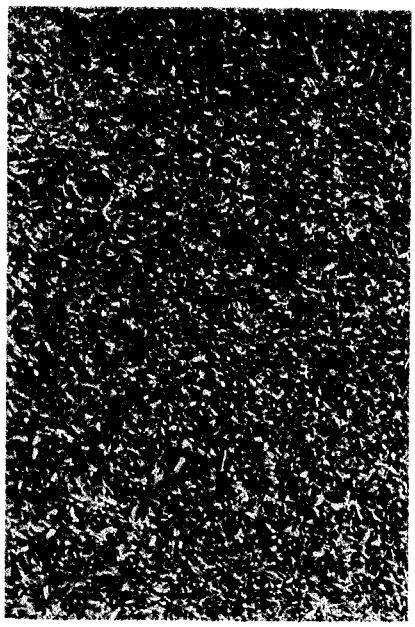
FIG. 1 is a photograph of 45176 St. Augustine turf showing generally the characteristics of this new grass.
Figure 2:
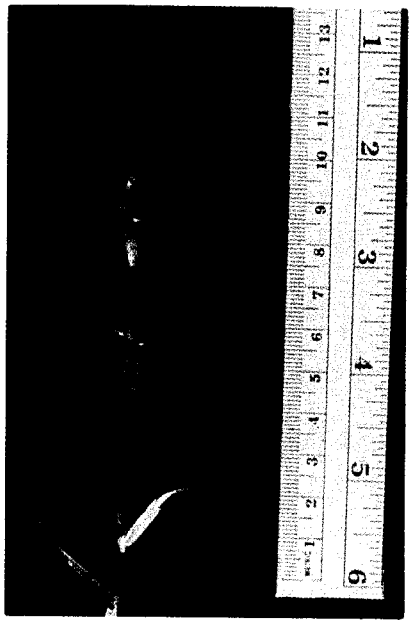
FIG. 2 shows the leaves and stem of a 45176 St. Augustinegrass plant.
Figure 3:
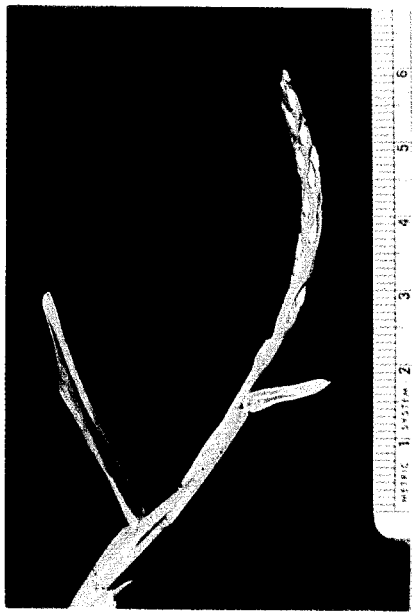
FIG. 3 shows a spike of a 45176 St. Augustinegrass plant.
Figure 4:
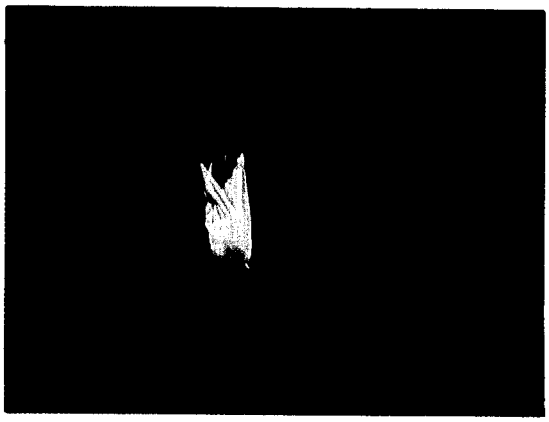
FIG. 4 shows a floret of a 45176 St. Augustinegrass plant.

Genotype 45176 possesses a moderate olive green color (7.5 GY 4/4) [1] and is characterized by compressed and branched culms. The leaf blades average 44.2 mm. long and average 6.04 mm. wide, with the average internode length 22.8 mm. The average leaf blade length and the average internode length, while shorter than other selections and varieties, are not as short as in 73176, thus allowing some differentiation between the two dwarfs. Genotype 45176 has a purple stigma color and an unreduced chromosome number of 18.

Total soluble salts measured in micromhos/cm. specific conductance using a Beckmann Solu-Bridge has given a reliable differentiation among some genotypes. The average reading for 45176 was 104.1 micromhos/cm. The chromosome numbers, stigma colors, morphological measurements, and specific conductance measurements of

[1] Munsell color designation obtained using a Nickerson color fan. The designated color is of plant material grown in the greenhouse. The color is subject to variation depending upon the environmental conditions under which the grass is grown.

45176 and other St. Augustinegrasses are compared in Tables 1, 2 and 3.

TABLE 1

Chromosome numbers and stigma colors of 45176 and other St. Augustinegrasses

| Selection/variety | Chromosome number (unreduced) [1] | Stigma color |
|---|---|---|
| 45176 | 18 | Purple. |
| 73176 | 18 | Do. |
| Ea611081 | 18 | Do. |
| Floratine | 27 | Do. |
| Bitter Blue | 27 | Do. |
| Texas Common | 18 | White. |

[1] Chromosome number determinations made on pollen mother cells.

TABLE 2

Comparative leaf blade length, width and internode length for 45176 and other St. Augustinegrasses

| Selection/variety | Leaf blade | | Internode length (mm.) [3] |
|---|---|---|---|
| | Length (mm.) [1] | Width (mm.) [2] | |
| 45176 | 44.2±11.8 | 6.04±0.89 | 22.8±3.8 |
| 73176 | 33.4±7.3 | 5.86±1.09 | 10.8±2.2 |
| Ea611081 | 78.4±33.3 | 7.12±1.38 | 36.0±7.4 |
| Floratine | 82.8±25.9 | 7.81±2.46 | 36.3±7.3 |
| Bitter Blue | 105.2±31.8 | 8.55±1.25 | 38.3±8.7 |
| Texas Common | 45.0±16.8 | 6.98±0.85 | 34.0±4.2 |
| LSD 5% | 12.1 | .71 | 4.0 |

[1] All plant material grown unclipped in greenhouse.
[2] Measurements recorded 15 millimeters above leaf collar.
[3] Measurements recorded between third and fourth internodes.

TABLE 3

Specific conductance measurements of 45176 and other St. Augustinegrasses

| Selection/variety | Specific conductance (micromhos/cm.) [1] |
|---|---|
| 45176 | 104.1 |
| 73176 | 107.3 |
| Ea611081 | 132.3 |
| Bitter Blue | 190.2 |
| Texas Common | 122.8 |

[1] Measurements were made on a six centimeter stem section.

Field observations of growth habit and texture at both the Apopka, Fla., and Katy, Tex. field stations demonstrate the dwarf characteristic of 45176 and the differences between 45176 and 73176. Clipping yield studies carried out during the summer, when St. Augustinegrass is most actively growing, can be relied upon to distinguish 45176 from other commercial and experimental St. Augustine grasses. This information is given in Tables 4, 5 and 6.

TABLE 4

Comparative growth habit averages for 45176 and other St. Augustinegrasses at Apopka, Florida and Katy, Texas

| Selection/variety | Growth habit [1] | | |
|---|---|---|---|
| | Florida 1971 | Texas 1971 | Florida 1972 |
| 45176 | 2.6 | 2.5 | 2.1 |
| 73176 | 2.4 | 2.5 | 1.6 |
| Ea611081 | 3.4 | 4.0 | 3.2 |
| Bitter Blue | 4.4 | 4.5 | 3.7 |
| Texas Common | | 4.5 | |
| LSD 5% | | | .2 |

[1] Rating 1=low growing; 5=upright growing.

TABLE 5

Comparative texture averages for 45176 and other St. Augustinegrasses at Apopka, Florida and Katy, Texas

| Selection/variety | Texture [1] | | |
|---|---|---|---|
| | Florida 1971 | Texas 1971 | Florida 1972 |
| 45176 | 2.7 | 2.1 | 3.0 |
| 73176 | 2.9 | 2.5 | 3.1 |
| Ea611081 | 1.7 | 2.0 | 2.3 |
| Bitter Blue | 1.4 | 1.5 | 2.0 |
| Texas Common | | 1.1 | |
| LSD 5% | | | .2 |

[1] Rating 4=fine texture; 1=course.

TABLE 6

Fresh weights of clippings removed from plots of 45176 and other St. Augustine grasses

| Selection/variety | Fresh weights (gms/.48 m.×1.52 m. plot) | | |
|---|---|---|---|
| | July | August | September |
| 45176 | 6.3±2.1 | 19.7±10.0 | 13.7±6.4 |
| 73176 | 3.0±1.7 | 6.0±3.6 | 7.7±2.9 |
| Ea611081 | 36.7±12.9 | 74.0±12.5 | 45.0±8.2 |
| Bitter Blue | 22.3±9.9 | 43.7±15.3 | 29.7±4.9 |
| LSD 5% | 16.6 | 21.8 | 11.0 |

The characteristic flowering shoot production and gray leafspot (*Piricularis grisea*) resistance, allow 45176 to be distinguished from genotype 73176. In both Texas and Florida, 45176 produced a greater amount of flowering shoots than 73176. Though 45176 produced an amount of flowering shoots equal to other non-dwarf St. Augustine grasses, the smaller size of the raceme made them less observable.

Genotype 45176, while having a level of gray leafspot resistance better than most other commercial St. Augustinegrasses, does not have resistance comparable to 73176. A summary of the flowering shoot production and gray leafspot resistance is given in Tables 7 and 8.

TABLE 7

Comparative ratings of average flowering shoot production of 45176 and other St. Augustinegrasses at Apopka, Florida and Katy, Texas

| Selection/variety | Average flowering shoot production [1] | |
|---|---|---|
| | Texas 9-17-71 | Florida 6-16-72 |
| 45176 | 3.0 | 2.3 |
| 73176 | 0 | .7 |
| Ea611081 | 0 | 2.0 |
| Bitter Blue | 0 | 1.3 |
| Texas Common | 3.0 | |
| LSD 5% | | 1.0 |

[1] Rating 0=No Flowering shoot production; 5=heavy flowering shoot production.

TABLE 8

Comparative gray leafspot (*Piricularis grisea*) resistance of 45176 and other St. Augustinegrasses at Apopka, Florida and Katy, Texas

| Selection/variety | Percent gray leafspot | | | | | |
|---|---|---|---|---|---|---|
| | Florida | | | Texas | | |
| | 6-28-71 | 4-31-71 | 6-29-71 | 7-31-71 | 9-2-71 | 9-17-71 |
| 45176 | 20 | 20 | 30 | 10 | 20 | 30 |
| 73176 | 20 | 10 | 10 | 20 | 5 | 0 |
| Ea611081 | 20 | 10 | 30 | 20 | 10 | 30 |
| Bitter Blue | 40 | 90 | 10 | 10 | 10 | 20 |
| Texas Common | | 10 | 60 | 20 | 30 | 20 |

Table 9 shows the high level of brownpatch (*Rhizoctonia solari*) resistance of 45176 when compared to other St. Augustinegrasses in a laboratory-greenhouse test. The results of this test could be relied upon to distinguish 45176 from other less resistant genotype.

TABLE 9

Comparative ratings of average brownpatch (*Rhizoctonia solani*) resistance of 45176 and other St. Augustinegrasses in laboratory-greenhouse test

| Selection/variety | Average brownpatch resistance [1] | |
|---|---|---|
| | 3-9-72 | 5-2-72 |
| 45176 | 3.7 | 3.0 |
| 73176 | 2.0 | 2.0 |
| Ea611081 | 2.7 | 2.7 |
| Bitter Blue | 2.3 | 2.3 |
| Floratine | 2.3 | 2.7 |

[1] Rating 1=at least brownpatch resistance; 4=most brownpatch resistance.

The cold hardiness of the dwarf 45176 allows identification when compared to other more vigorous, cold hardy St. Augustinegrasses. Genotype 45176 will not tolerate below zero centigrade temperatures as well, though some added protection is available at near zero temperatures through a reduction in the thatch layer. This information is given in Table 10.

TABLE 10

Comparative cold damage from below zero (centigrade) temperatures of 45176 and other St. Augustinegrasses in Apopka, Florida and Katy, Texas

| Selection/variety | Percent cold damage [1] | | |
|---|---|---|---|
| | | Florida 1973 | |
| | Texas 1972 | Test A [2] | Test B [3] |
| 45176 | 95 | 60 | 47.5 |
| 73176 | 99 | 40 | 35.0 |
| Ea611081 | 99 | 15 | 50.0 |
| Bitter Blue | 20 | 5 | 52.5 |
| Texas Common | 0 | | |

[1] Cold damage as measured by percent stolons killed.
[2] Test A.—Two year old sod.
[3] Test B.—One year old sod.

Table 11 compares morphological characteristics of spikelets of 45176 with other St. Augustinegrasses.

TABLE 11

Comparative morphological characteristics of spikelets on 45176 and other St. Augustinegrasses

| Selection/variety | Length of— | | | |
|---|---|---|---|---|
| | First glume [1] (mm.) | Second glume (mm.) | Lemma (mm.) | Palea (mm.) |
| 45176 | .95±.15 | 3.72±.13 | 3.24±.16 | 2.80±.09 |
| 73176 | 1.04±.10 | 3.96±.14 | 3.68±.13 | 3.29±.15 |
| Ea 611081 | 1.08±.08 | 3.99±.14 | 3.58±.21 | 3.24±.18 |
| Texas Common | .99±.11 | 3.99±.18 | 3.67±.21 | 3.20±.12 |
| LSD 5% | .07 | .06 | .12 | .09 |

[1] Measurements recorded in millimeters using 12.5× magnification.

What is claimed and desired to be secured by Letters Patent is:

1. St. Augustinegrass, substantially as herein illustrated and described.

References Cited

UNITED STATES PATENTS

P.P. 2,863 2/1969 Long ---------- Plants—88

ROBERT E. BAGWILL, Primary Examiner